United States Patent [19]
Hirao

[11] Patent Number: 5,333,610
[45] Date of Patent: Aug. 2, 1994

[54] ABSORPTION SPECTRUM DETERMINING METHOD AND SPECTROMETRIC MEASURING APPARATUS FOR LIGHT-DIFFUSIVE OBJECT USING THE METHOD

[75] Inventor: Konomu Hirao, Osaka, Japan

[73] Assignee: Otsuka Electronics Co., Ltd., Osaka, Japan

[21] Appl. No.: 857,954

[22] Filed: Mar. 26, 1992

[30] Foreign Application Priority Data

Mar. 27, 1991 [JP] Japan ................................. 4-63308

[51] Int. Cl.$^5$ ............................................. A61B 5/00
[52] U.S. Cl. ................................. 128/633; 128/664; 128/665; 356/39; 356/300; 356/326
[58] Field of Search .......................... 128/633–634, 128/664–665; 356/300, 326, 328, 39–41

[56] References Cited

U.S. PATENT DOCUMENTS 3,794,425  2/1974  Smith et al.
4,321,930  3/1982  Jobsis et al.

FOREIGN PATENT DOCUMENTS 2075668  11/1981  United Kingdom .
2228568  2/1990  United Kingdom .

Primary Examiner—Angela D. Sykes
Attorney, Agent, or Firm—Sughrue, Mion, Zinn, Macpeak & Seas

[57] ABSTRACT

Using optical measurement data obtained from a light-diffusive object the percentage absorption %ABS of the object is calculated, and using one constant or a multiple constant $n_i$ ($_i=1,2,\ldots$) the spectrum waveform is calculated according the equation as follows:

$$S(\lambda) = \exp[n \cdot \%ABS(\cdot)]$$

or the equation as follows:

$$S(\lambda) = \Sigma \exp[n_i \cdot \%ABS(\cdot)]$$

whereby a spectrum waveform nearly equal to the spectrum waveform of the inherent percentage absorption of the light-diffusive object can be obtained. By carrying out a spectrum analysis of a light-diffusive object by means the spectrum waveform $S(\lambda)$, the components of the object can be analyzed with high reproducibility and reliability without slicing or shattering the object.

4 Claims, 10 Drawing Sheets

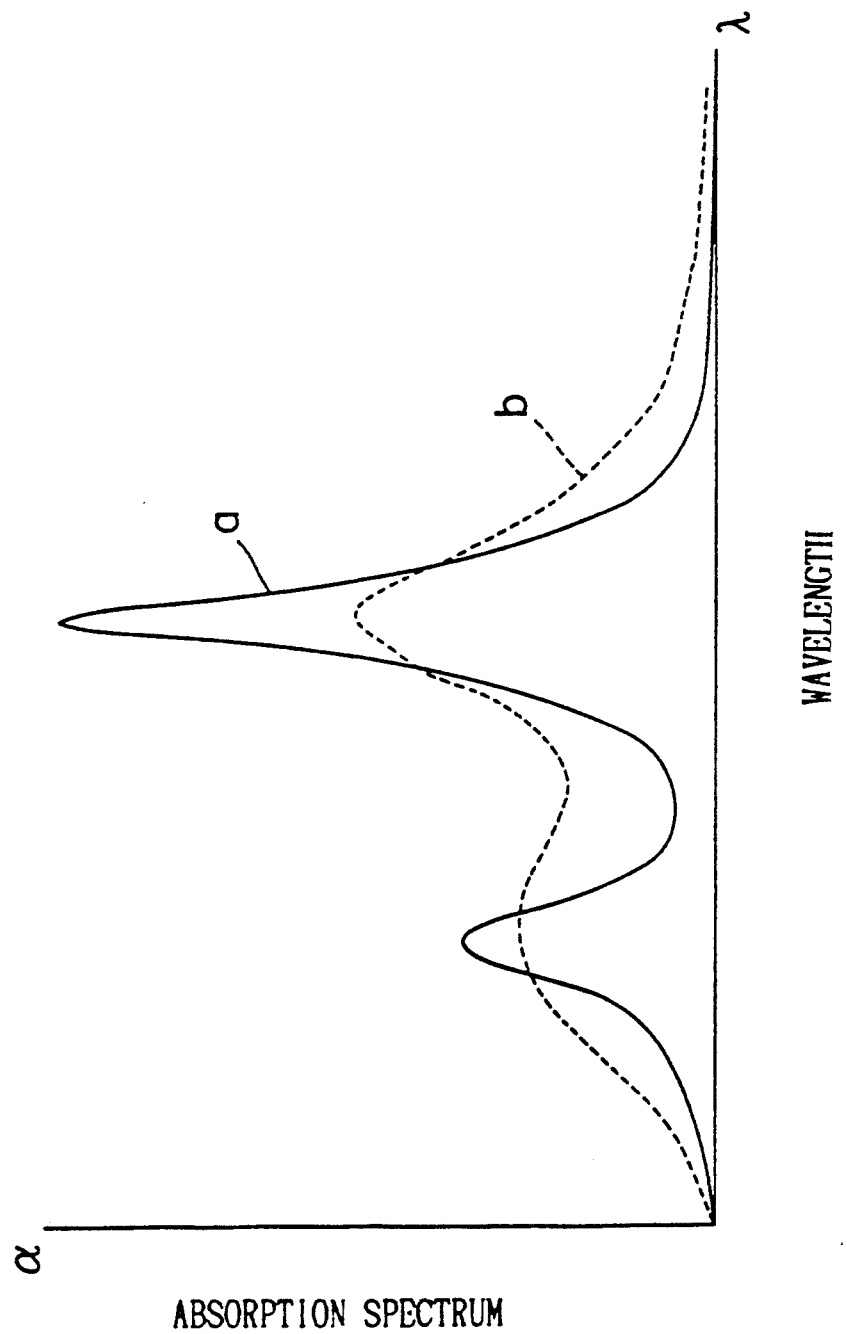

ABSORPTION SPECTRUM DETERMINING METHOD AND SPECTROMETRIC MEASURING APPARATUS FOR LIGHT-DIFFUSIVE OBJECT USING THE METHOD

BACKGROUND OF THE INVENTION

The present invention relates to an absorption spectrum determining method which is capable of correctly obtaining the absorption spectrum waveform of an object by applying light from a surface of the object to inside of the object and receiving light which has diffused and reflected as passing through inside of the object at least at one point on the surface of the object and a spectrometric measuring apparatus for a light-diffusive object using the method.

Conventionally in carrying out a quantitative analysis for an object according to an absorptiometric method, when the object to be measured is fluid or gas, the transmissivity of light has been able to be measured because light passes through the object. However, when measuring an opaque object, light does not sufficiently pass through the object, therefore, the object to be measured has been preliminarily sliced or shattered to pieces before being subject to measurement of The absorption spectrum thereof.

However, the above-mentioned method cannot De adopted for measuring a living body alive. In view of the above, there is disclosed the method of applying light onto a surface of an object and receiving reflected light at another point on the same surface of the object to carry out certain calculations based on data of received light for consequently measuring information inside the object (for example, refer to the official bulletin of Japanese Patent Publieation No. 11614/1986(B)).

According to the above-mentioned method, light is conducted to a measurement point of a living body by means of a light emitting device to collect light which has diffused or reflected as passing through the living body, therefore, a continuous measurement can be carried out with the internal organs located at their proper positions inside the living body without inserting any part of the measuring device nor injuring the living body.

However, usually the object to be measured is not a transparent body but so-called a light-diffusive object which reflects or diffuses light in FIG. 9. In a light-diffusive object, reflection and refraction of light repeal many times in the light-diffusive object even when the distance between the light applying point A and the light receiving point B is fixed.

For the above reasons, when carrying out measurement with light application onto the surface of a light-diffusive object of the above-mentioned kind, a phenomenon of broadened absorption spectrum waveform results due to the distribution of substantial optical path length. FIG. 10 shows a graph of the above-mentioned phenomenon where the peak of the absorption spectrum waveform b measured from a surface of the object is weakened as compared with the inherent spectrum waveform a obtained through measurement by slicing the object.

The above fact has also resulted in the problem that, if carrying out an analysis of the components of the object using the measured light transmission data based on a weakened absorption spectrum waveform of the above kind, correct data has not been obtained.

Accordingly, it is an object of the present invention to provide an absorption spectrum correcting method and a spectrometric measuring apparatus using the method for measuring a light-diffusive object, the method and apparatus being capable of obtaining data of a curve similar to the inherent absorption spectrum waveform of the object by correcting an absorption spectrum waveform measured without shattering or processing the light-diffusive object when measuring the internal information the object by applying light to a light applying point on a surface of the object and receiving light which has passed through inside of the object at a light receiving point of the object to carry out an absorption spectrum analysis based on data of received light.

SUMMARY OF THE INVENTION

In order to achieve the above-mentioned object, an absorption spectrum correcting method in accordance with the present invention comprises the steps of detecting the intensity I of light received at a light receiving point at each wavelength $\lambda$, obtaining the percentage absorption %ABS ($\lambda$) with the reference light intensity assumed to be Io as follows:

$$\%ABS\,(\lambda) = (Io - I)/Io,$$

and obtaining the value S($\lambda$) using one constant n as follows:

$$S(\lambda) = exp\,[n \cdot \%ABS\,(\lambda)]$$

or obtaining the value S($\lambda$) using a multiple constant $n_i$ ($i = 1, 2, \ldots$) as follows:

$$S(\lambda) = \Sigma exp\,[n_i \cdot \%ABS\,(\lambda)]$$

whereby the spectrum waveform of the inherent percentage absorption of the object is expressed by the above value S($\lambda$).

The spectrometric measuring apparatus using the above-mentioned absorption spectrum correcting method in accordance with the present invention comprises light emitting means for emitting light onto a light applying point on a surface of an object, light receiving means for receiving light which has passed through inside of the object at a light receiving point of the object, calculation means for calculating, by detecting the intensity of light received at the light receiving point at each wavelength with the reference light intensity assumed to be Io, the percentage absorption %ABS as follows:

$$\%ABS(\lambda) = (Io - I)/Io,$$

and calculation means for calculating the spectrum waveform S($\lambda$) using one constant n according to the equation as follows:

$$S(\lambda) = exp\,[n \cdot \%ABS(\lambda)]$$

or calculation means for calculating the spectrum waveform S($\lambda$) using a multiple constant $n_i$ ($i = 1, 2, \ldots$) according to the equation as follows:

$$S(\lambda) = \Sigma exp[n_i \cdot \%ABS\,(\lambda)]$$

whereby the spectrum waveform of the inherent percentage absorption of the object can be obtained according to the calculated result of spectrum waveform $S(\lambda)$.

According to the above-mentioned absorption spectrum correcting method and spectrometric measuring apparatus, the percentage absorption %ABS of a specimen is calculated from the optical measurement data of the specimen, and one constant or a multiple constant $n_i$ ($i=1,2,\ldots$) is set up to calculate the spectrum waveform $S(\lambda)$:

$$S(\lambda) = exp\,[n \cdot \%ABS\,(\lambda)]$$

or the spectrum waveform $S(\lambda)$:

$$S(\lambda) = \Sigma exp\,[n_i \cdot \%ABS\,(\lambda)]$$

A certain finite number K of such constants are used in the multiple constant situation, such a finite number being selectable by the user.

The spectrum waveform $S(\lambda)$ has a waveform similar to the spectrum waveform of the inherent percentage absorption of the light-diffusive object.

Therefore, a correct spectrum analysis of the object can be carried out by means of the spectrum waveform $s(\lambda)$.

According to the above-mentioned absorption spectrum correcting method and spectrometric measuring apparatus of the present invention, the percentage absorption %ABS of a specimen is calculated from the optical measurement data of the specimen, and one constant or a multiple constant $n_i$ ($i=1,2,\ldots$) is set up to calculate the spectrum waveform $S(\lambda)$:

$$S(\lambda) = exp\,[n \cdot \%ABS\,(\lambda)]$$

or the spectrum waveform $S(\lambda)$:

$$S(\lambda) = \Sigma\,exp\,[n_i \cdot \%ABS\,(\lambda)]$$

to enable obtaining a spectrum waveform nearly equal to the spectrum waveform of the inherent percentage absorption of the light-diffusive object.

Therefore, by carrying out a spectrum analysis of a light-diffusive object by means of the spectrum waveform $S(\lambda)$, the components of the object can be analyzed with high reproducibility and reliability without slicing or shattering the object.

Particularly when a multiple constant $n_i$ ($i=1,2,\ldots$) is set up to calculate the spectrum waveform $S(\lambda)$:

$$S(\lambda) = \Sigma exp\,[n_i \cdot \%ABS\,(\lambda)]$$

a spectrum waveform closest to the spectrum waveform of the inherent percentage absorption of the light-diffusive object can be obtained.

The above object and other features will be more apparent with reference to the attached drawings.

BRIEF DESCRIPTION OF THE DRAWINGS

FIG. 10 is a graph where an absorption spectrum waveform b obtained through measurement with light application onto the surface of the light-diffusive object in FIG. 9 is compared with the inherent absorption spectrum waveform a of the object.

DETAILED DESCRIPTION OF THE PREFERRED EMBODIMENTS

Figure 1:
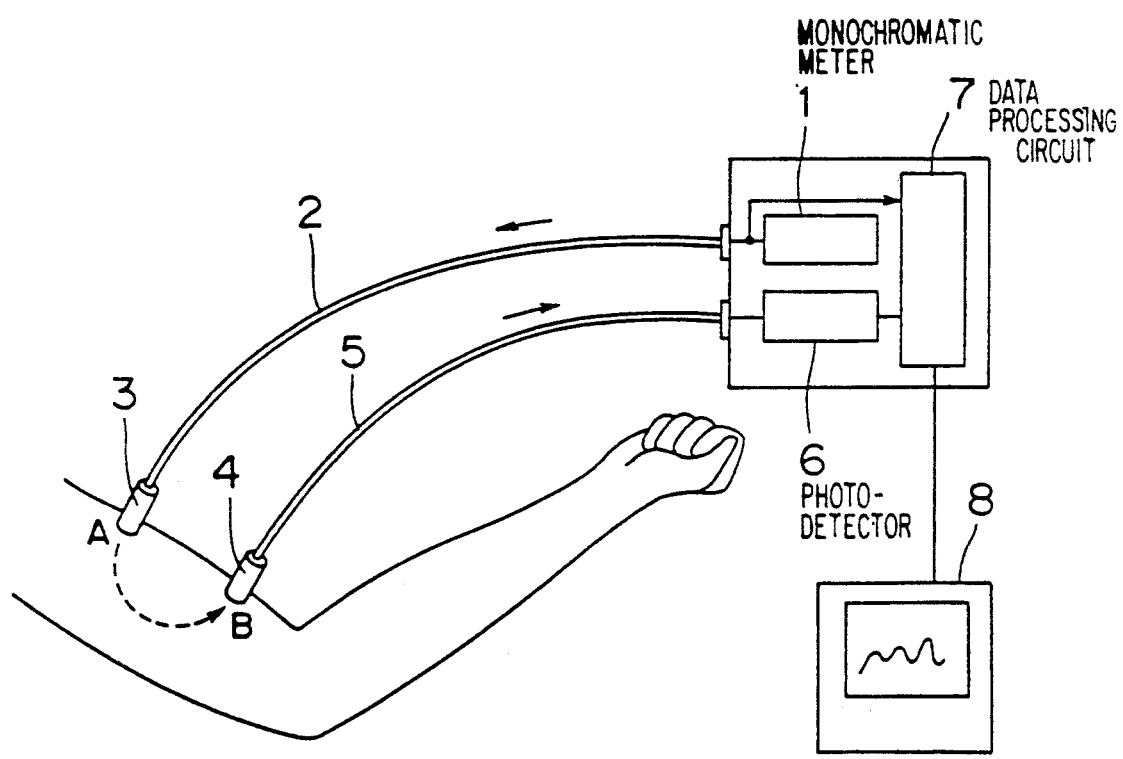
FIG. 1 is an explanatory view of a spectrometric measuring apparatus for light-diffusive object in accordance with an embodiment of the present invention.

FIG. 1 is an explanatory view of an embodiment of the present invention. Firstly, a light applying end 3 of an optical fiber 2 and a light receiving end 4 of an optical fiber 5 for receiving light which is applied from the light applying end and diffused in a living body are put close respectively to a light applying point A and a light receiving point B on a surface of the living body. There is a certain distance between the light receiving point B and the light applying point A so that the intensity of light to be input to the light receiving end 4 can be sufficient and the influence of light transmitted along the surface of the living body tissue can be ignored. In other words, when the distance between the light receiving point B and the light applying point A is too great, the intensity of light input from the light applying end 3 into the light receiving end 4 reduces to result in deteriorating the signal-to-noise ratio at measurement. However, when the distance between the light receiving point B and the light applying point A is too small, light applied from the light applying end 3 enters directly through the surface of the living body tissue into the light receiving end 4 to result in relatively weakening the measurement signal. In order to eliminate possible influence of reflected light, it is desirable that the directivity of each of the light applying end 3 and the light receiving end 4 is as narrow as possible. However, when the directivity of each end is too narrow, almost all of light applied from the light applying end 3 enters into inside of the living body to result in hardly securing the amount of light reaching the light receiving end 4.

The light applying end 3 is connected by way of the optical fiber 2 to a monochromatic meter 1, while the light receiving end 4 is connected to a photodetector 6 by way of the optical fiber 5. The photodetector 6 forms an output to a data processing circuit 7 and a spectrum display unit 8.

Describing in more detail, the monochromatic meter 1 comprises a spectroscopic element such as a white light source, a prism, or a diffraction grating to output light at a desired wavelength. The light applying end 3 comprises a light converging member ( e.g., lens ) for conducting light emitted out of the optical fiber. The light receiving end 4 also comprises a light converging member. The photodetector 6 has a built-in light intensity detecting element such as a photo-transistor.

It is noted that, although the light converging member faces the living body tissue via a gap in the above-mentioned embodiment ( refer to FIG. 2 ), the light converging member can be put in contact with the living body tissue.

Figure 2:
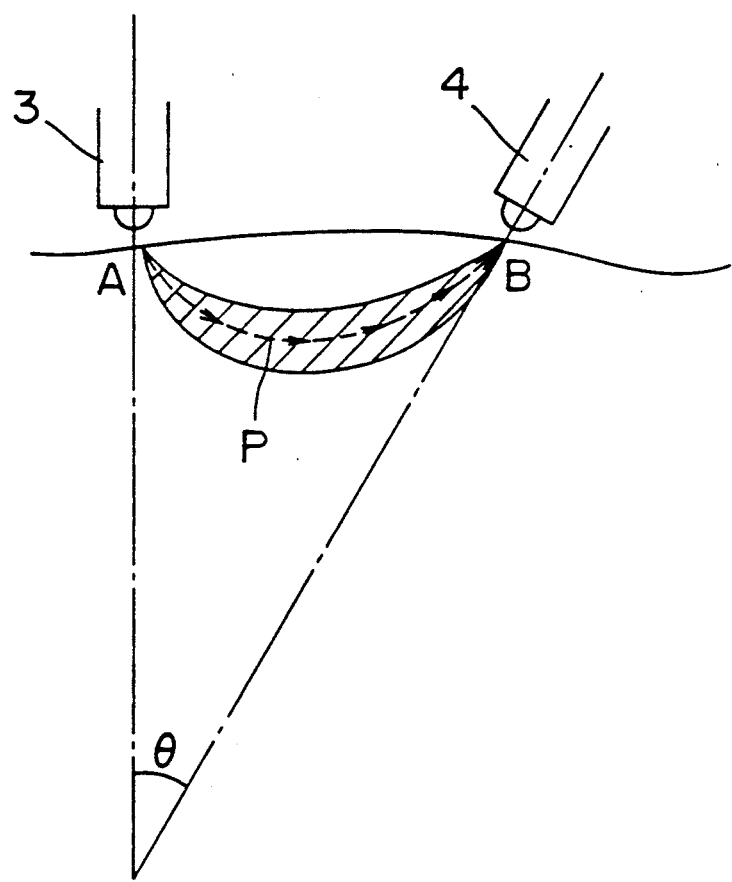
FIG. 2 is a section view of the measurement point of a living body.

Monochromatic light emitted from the light applying end 3 enters into inside of the living body. A part of light travels inside the living body as shown in FIG. 2 to consequently reach the light receiving point B. In more detail, a part of light which is emitted from the light applying end 3 and received at the light receiving end 4 as detectable light passes through inside of the living body as diffusing and diverging. The area through which light passes as diffusing is indicated by the hatched area in FIG. 2. In the area through which light diffuses a path through which a greatest part of light passes, i.e., the center point of energy distribution of the flux of light or the locus of average points of light which travels as diffusing (the substantial diffused light path referred to merely as the "diffused light path" hereinafter) is represented by a symbol P.

Light emitted from the light applying end 3 and input to the light receiving end 4 has information inside of the living body between the light applying point A and the light receiving point B.

The photodetector 6 detects light emitted from the light applying end 3 and input to the light receiving end 4 and forms a signal input to the data processing circuit 7. The data processing circuit 7 receives the intensity signal of monochromatic light emitted from the monochromatic meter 1 as a reference and carries out prescribed calculations based on the difference between the above-mentioned two detection signals to obtain an absorption spectrum data representative of the internal condition of the living body between the points A and B. The following describes the calculation procedures in detail.

Postulating that the intensity of light detected by the photodetector 6 at each wavelength is I and the reference light intensity is Io, the percentage absorption %ABS is obtained as follows:

$$\%ABS = (Io - I)/Io$$

wherein %ABS is a function of wavelength ($\lambda$).

By using an appropriate value (a positive real number), the following calculation is carried out.

$$S(\lambda) = \exp[n \cdot \%ABS(\lambda)]$$

or using appropriate constants $n_1$ and $n_2$ (positive real numbers), the following calculation is carried out.

$$S(\lambda) = \exp[n_1 \cdot \%ABS(\pi)] + \exp[n_2 \cdot \%ABS(\lambda)]$$

wherein the dot mark "·" represents multiplication and the values $n_1$ and $n_2$ are numbers independent of wavelength $\lambda$.

The value $S(\lambda)$ calculated as above approximately corresponds to a curve obtained by expressing the inherent absorption spectrum in the percentage absorption form. Therefore, the inherent absorption spectrum of the object can be obtained based on the value $S(\lambda)$. Particularly when the object is a multicomponent system (a system including a multiplicity of components exhibiting different spectrums, for example, blood including Hb and HbO$_2$), a multicomponent analysis by means of spectrum can be carried out correctly.

The following describes the results of an experiment.

Figure 3:
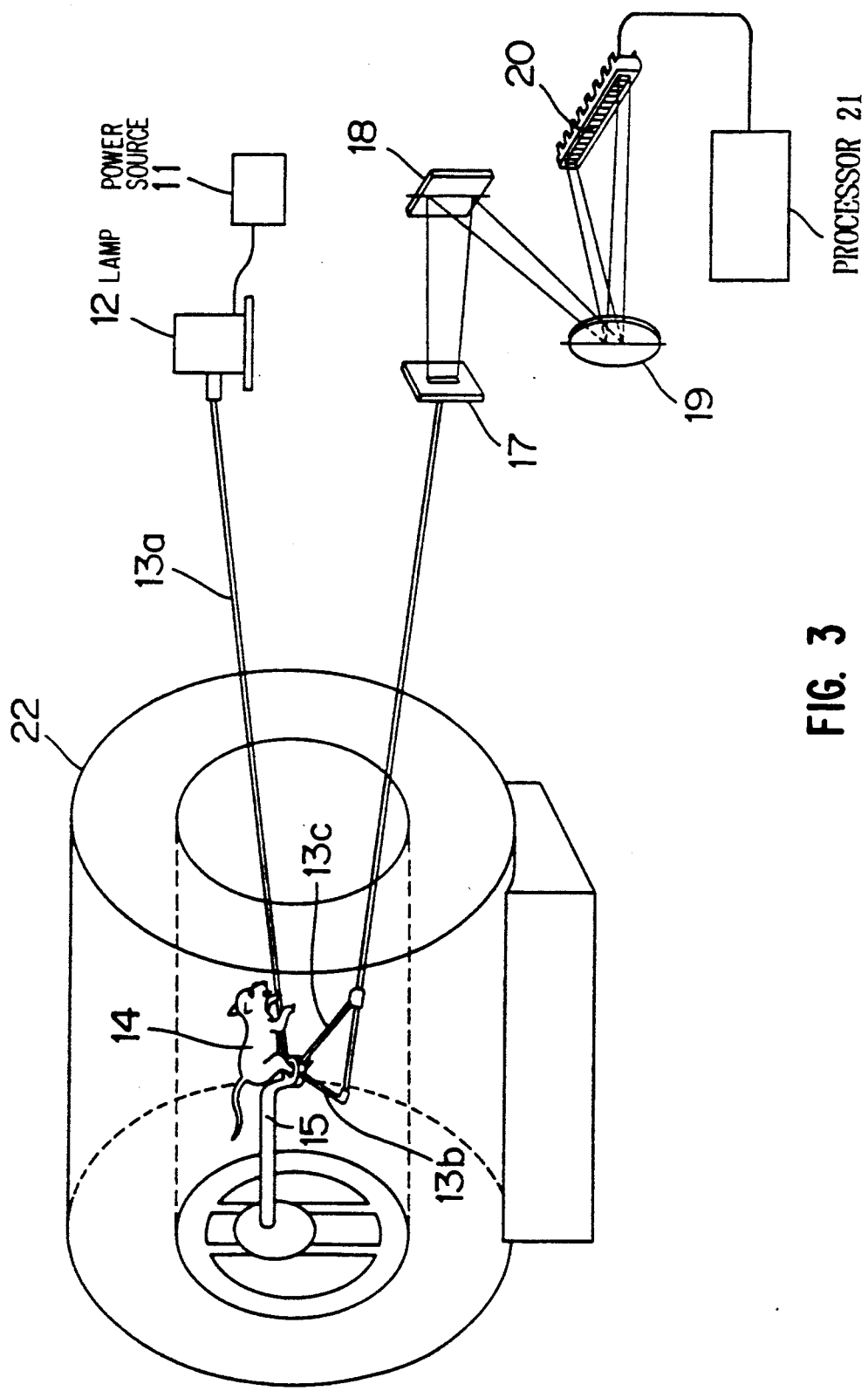
FIG. 3 is an explanatory view of a spectrometric measuring apparatus used for a test for correcting the absorption spectrum.

FIG. 3 shows an experimental apparatus for measuring the femoral muscle of a rat.

Figure 4:
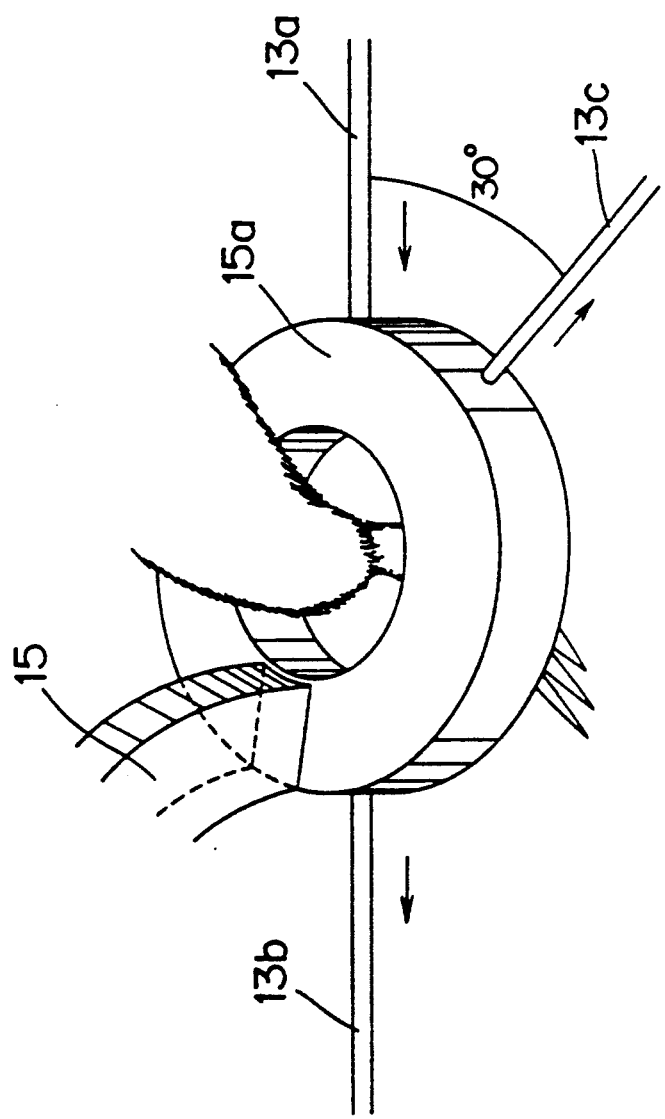
FIG. 4 is an enlarged view of a portion of a leg of a rat to which light is applied.

A living rat 14 is put in a vessel 22 and a hind leg of the rat 14 is fixed to a support member 15. The fixation condition of the hind leg of the rat 14 is shown in FIG. 4. The hind leg of the rat 14 is inserted through a ring 15a provided at the tip end portion of the support member 15. Into the ring 15a are also inserted the tip end portions of an incident light fiber 13a, a transmitted light fiber 13b, and a diffused light fiber 13c. The tip end portion of the transmitted light fiber 13b and the tip end portion of the diffused light fiber 13c makes an angle of 30° therebetween. The incident light fiber 13a conducts light emitted from an I$_2$ lamp connected to a power source 11, while the transmitted light fiber 13b picks up light which has passed through the hind leg of the rat 14. In the following description of the experiment, light picked up by the transmitted light fiber 13b is referred to as the "transmitted light", and light picked up by the diffused light fiber 13b is referred to as the "diffused light". The transmitted light is light which outgoes in the same direction as that of incident light after passing through the hind leg of the rat 14 as being transmitted and refracted in the hind leg. The absorption spectrum of transmitted light can be assumed to have the same form as that of the inherent absorption spectrum of the object. The diffused light is light which outgoes in a direction different from that of incident light after passing through the hind leg of the rat 14 as being reflected and refracted in the hind leg. The absorption spectrum of reflected light is weakened and flattened as compared with the inherent absorption spectrum of the object. Presumably, the reason of the above is that the above-mentioned substantial diffused light path bends and there are greater amount of reflected diffused light components rearward of light.

Transmitted light from the transmitted light fiber 13b and diffused light from the diffused light fiber 13c are selected by means of an optical switch (not shown) to be incident light input via a slit 17 and a mirror 18 to a diffraction grating 19. Diffused light from the diffraction grating 19 is received by a unidimensional image sensor 20.

When applying light from the I$_2$ lamp to the hind leg of the rat 14 in the above-mentioned measuring system, light spreads in many directions inside the hind leg, and a part of light is picked up by the transmitted light fiber 13b and the diffused light fiber 13c. Transmitted light or diffused light is separated by the diffraction grating 19, and an image corresponding to the intensity absorption spectrum is focused on the light receiving surface of the unidimensional image sensor 20. Electric charge accumulated in proportion to the focus intensity on the light receiving surface is converted into a time series image signal via a signal transfer electrode to be input to a processor 21 where the following signal processing is carried out.

Firstly, the transmission intensity T and the diffusion intensity D of objective light conducted by way of the transmitted light fiber 13b and the diffused light fiber 13c are measured at each wavelength.

Secondly a test tube containing yogurt adopted as an example of a light-diffusive object is inserted in the ring 15a instead of the hind leg of the rat 14, and the transmission intensity $T_o$ and the diffusion intensity $D_o$ of reference light conducted by way of the transmitted light fiber 13b and the diffused light fiber 13c are measured.

Then the transmission coefficient $\alpha_T$ and the diffusion coefficient $\alpha_D$ are calculated as follows:

$$\alpha_T = \log(T_0/T)$$

$$\alpha_D = \log(D_0/D)$$

Furthermore, the percentage absorption $\%ABS_T$ of transmitted light is obtained as follows:

$$\%ABS_T = (T_0 - T)/T_0$$

and the percentage absorption $\%ABS_D$ of diffused light is obtained as follows:

$$\%ABS_D = (D_0 - D)/D_0$$

Furthermore, the percentage absorption $\%ABS_D$ of diffused light is standardized through subtraction at the reference wavelength of 758 nm to obtain a standardized value n-$\%ABS_D$, and the standardized value n-$\%ABS_D$ is subject to correction according to the equations:

$$S_{Dn1} = \exp[1.927 \cdot n - \%ABS_D] \quad (1)$$

$$S_{Dn2} = \exp[0.827 \cdot n - \%ABS_D] \quad (2)$$

or according to the equation:

$$S_{Dn1,n2} = \exp[1.927 \cdot n - \%ABS_D] + \exp[0.827 \cdot n - \%ABS_D] \quad (3)$$

Calculation results of the above equations are shown in Table 1.

TABLE 1

| Wavelength | $\alpha_T$ | $\alpha_D$ | % ABS$_T$ | % ABS$_D$ | S$_{Dn1}$ | S$_{Dn2}$ | S$_{Dn1,n2}$ | n-S$_{Dn1+n2}$ |
|---|---|---|---|---|---|---|---|---|
| 600 | 1.837 | 1.651 | 0.985 | 0.978 | 1.610 | 1.227 | 2.836 | 1.836 |
| 620 | 1.227 | 1.123 | 0.941 | 0.925 | 1.453 | 1.174 | 2.628 | 1.628 |
| 640 | 0.895 | 0.924 | 0.873 | 0.881 | 1.336 | 1.132 | 2.468 | 1.468 |
| 660 | 0.754 | 0.842 | 0.824 | 0.856 | 1.273 | 1.109 | 2.383 | 1.383 |
| 680 | 0.584 | 0.743 | 0.739 | 0.819 | 1.186 | 1.076 | 2.262 | 1.262 |
| 700 | 0.415 | 0.643 | 0.616 | 0.773 | 1.084 | 1.035 | 2.120 | 1.120 |
| 720 | 0.314 | 0.575 | 0.515 | 0.734 | 1.006 | 1.003 | 2.008 | 1.008 |
| 740 | 0.270 | 0.551 | 0.463 | 0.719 | 0.978 | 0.990 | 1.968 | 0.968 |
| 760 | 0.312 | 0.570 | 0.513 | 0.731 | 1.000 | 1.000 | 2.000 | 1.000 |
| 780 | 0.230 | 0.517 | 0.410 | 0.695 | 0.934 | 0.971 | 1.905 | 0.905 |
| 800 | 0.194 | 0.485 | 0.361 | 0.673 | 0.894 | 0.953 | 1.847 | 0.848 |
| 820 | 0.187 | 0.482 | 0.349 | 0.670 | 0.891 | 0.951 | 1.842 | 0.842 |
| 840 | 0.185 | 0.490 | 0.347 | 0.677 | 0.901 | 0.956 | 1.858 | 0.858 |
| 860 | 0.183 | 0.492 | 0.344 | 0.678 | 0.903 | 0.957 | 1.861 | 0.861 |
| 880 | 0.183 | 0.499 | 0.343 | 0.683 | 0.912 | 0.961 | 1.873 | 0.873 |
| 900 | 0.172 | 0.512 | 0.327 | 0.693 | 0.929 | 1.000 | 1.929 | 0.929 |

Figure 5:
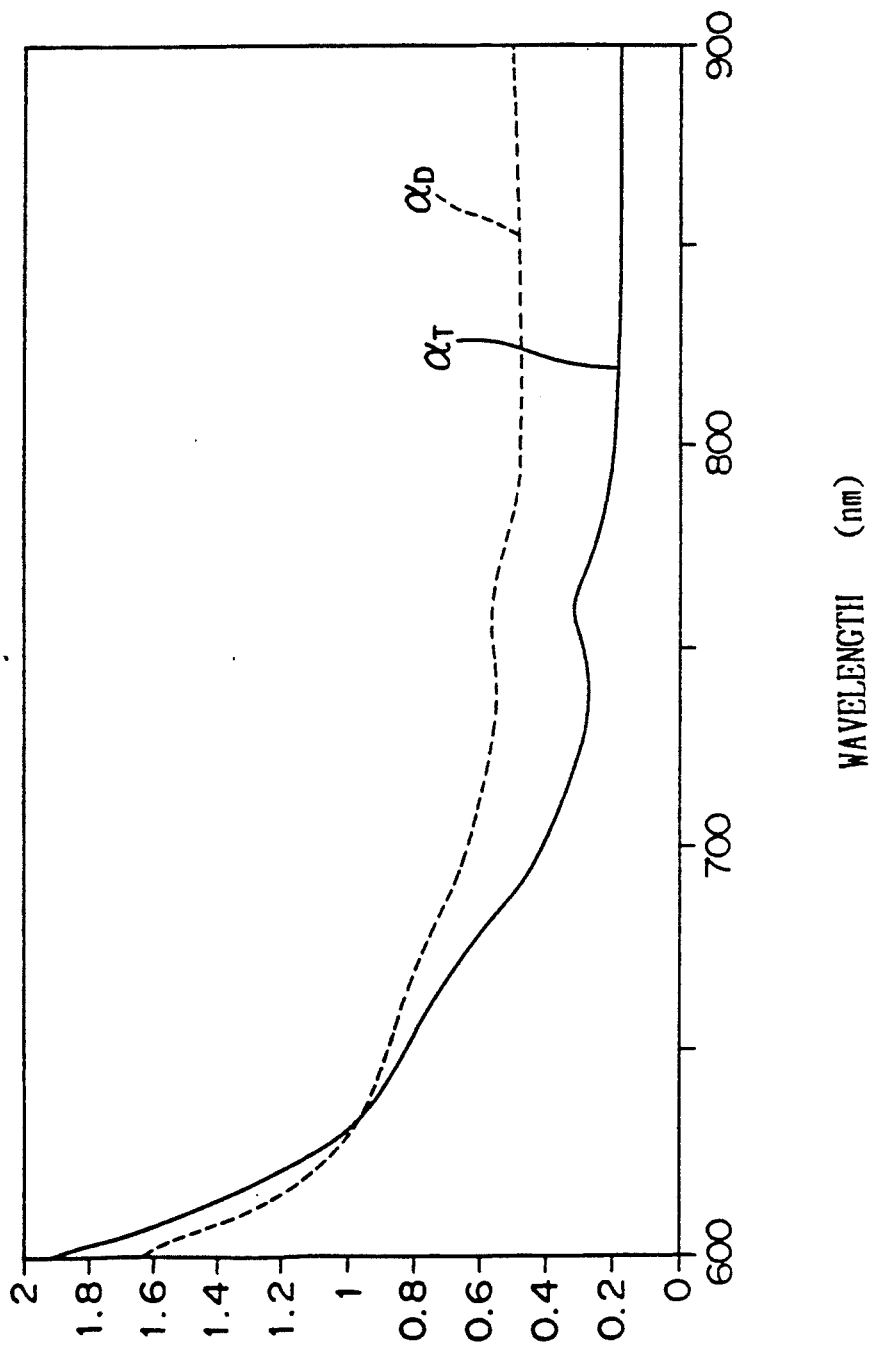
FIG. 5 is a graph of a transmission coefficient $a_T$ and a diffusion coefficient $a_D$ obtained through an experiment.

FIG. 5 shows a graph of the transmission coefficient $\alpha_T$ and the diffusion coefficient $\alpha_D$ picked up from Table 1. Referring to FIG. 5, the waveform of the diffusion coefficient $\alpha_D$ has a low peak and a lifted flat portion as compared with the waveform of the transmission coefficient $\alpha_T$.

Figure 6:
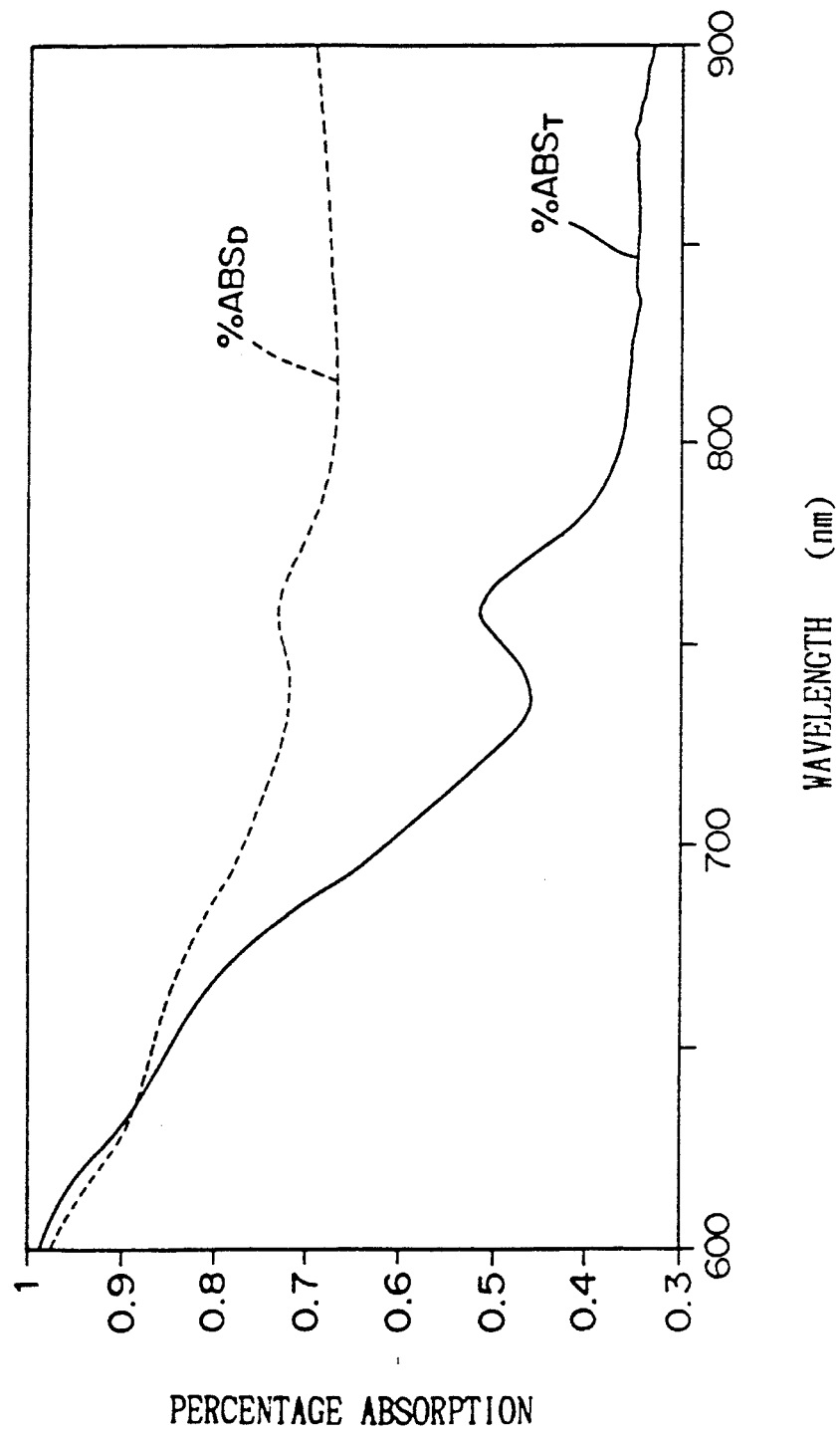
FIG. 6 is a graph of the percentage absorption %$ABS_T$ of transmitted light and the percentage absorption %$ABS_D$ of diffused light.

FIG. 6 shows a graph of the percentage absorption $\%ABS_T$ of transmitted light and the percentage absorption $\%ABS_D$ of diffused light picked up from Table 1.

Figure 7:
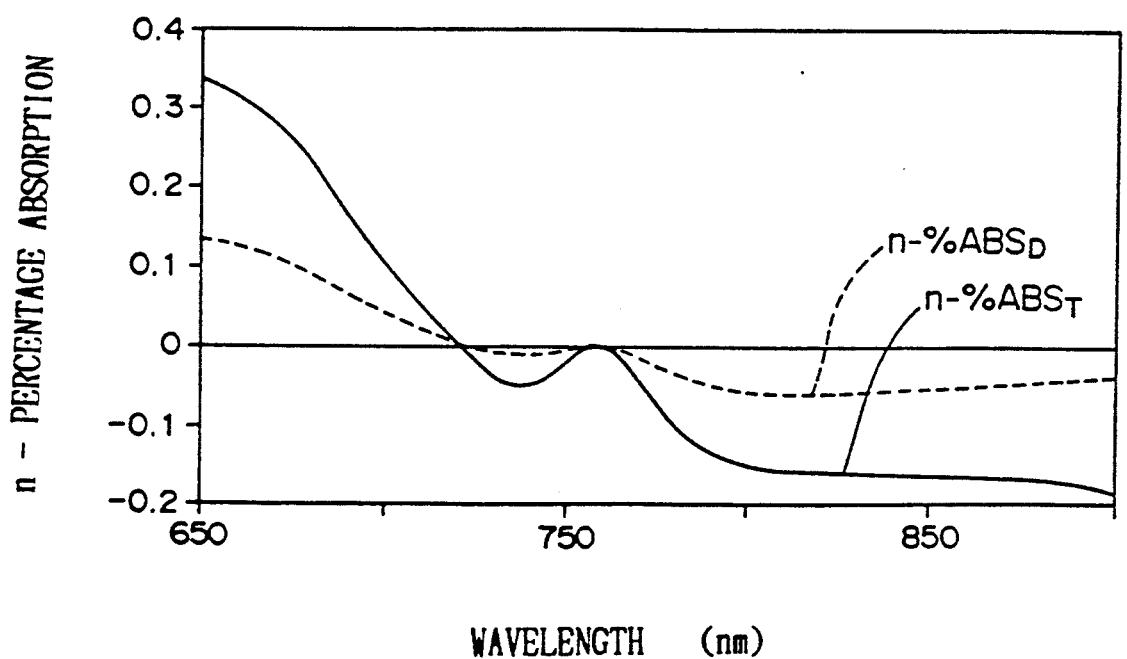
FIG. 7 is a graph where the percentage adsorption %$ABS_T$ of transmitted light and the percentage adsorption %$ABS_D$ of diffused light are adjusted at the peak of 758 nm.

FIG. 7 shows a graph where n-$\%ABS_T$ and n-$\%ABS_D$ obtained by standardizing respectively the percentage absorption $\%ABS_T$ of transmitted light and the percentage absorption $\%ABS_D$ of diffused light with the values at the wavelength 758 nm adjusted to 0.

Figure 8:
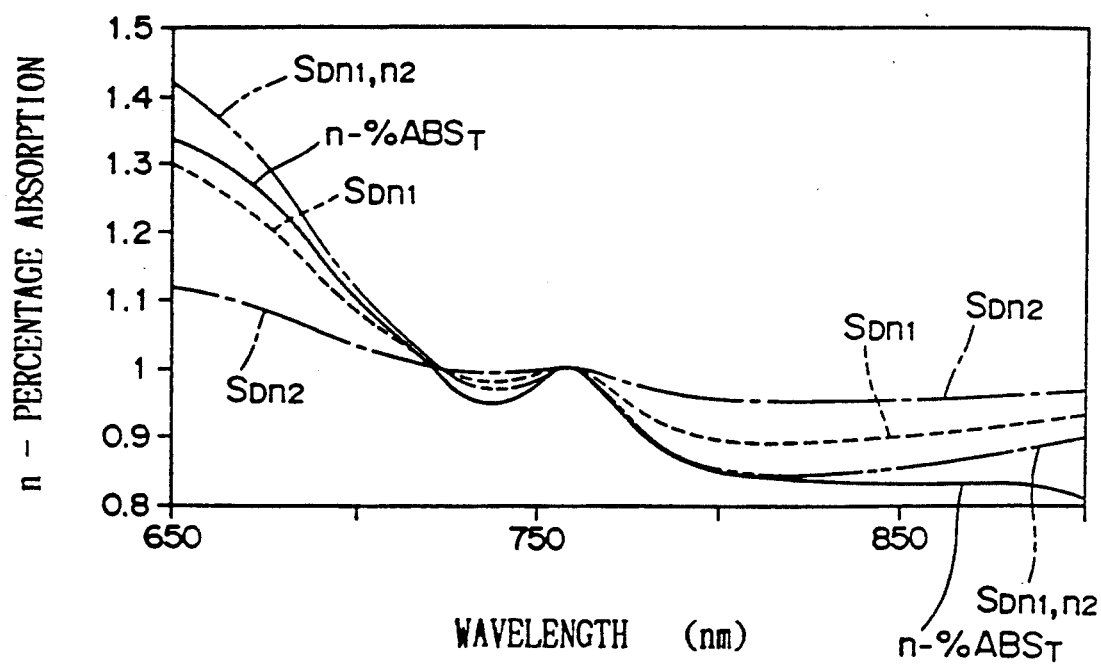
FIG. 8 is a graph where the percentage absorption %$ABS_D$ of diffused light is corrected by means of correction equations (1), (2), and (3).
Figure 9:
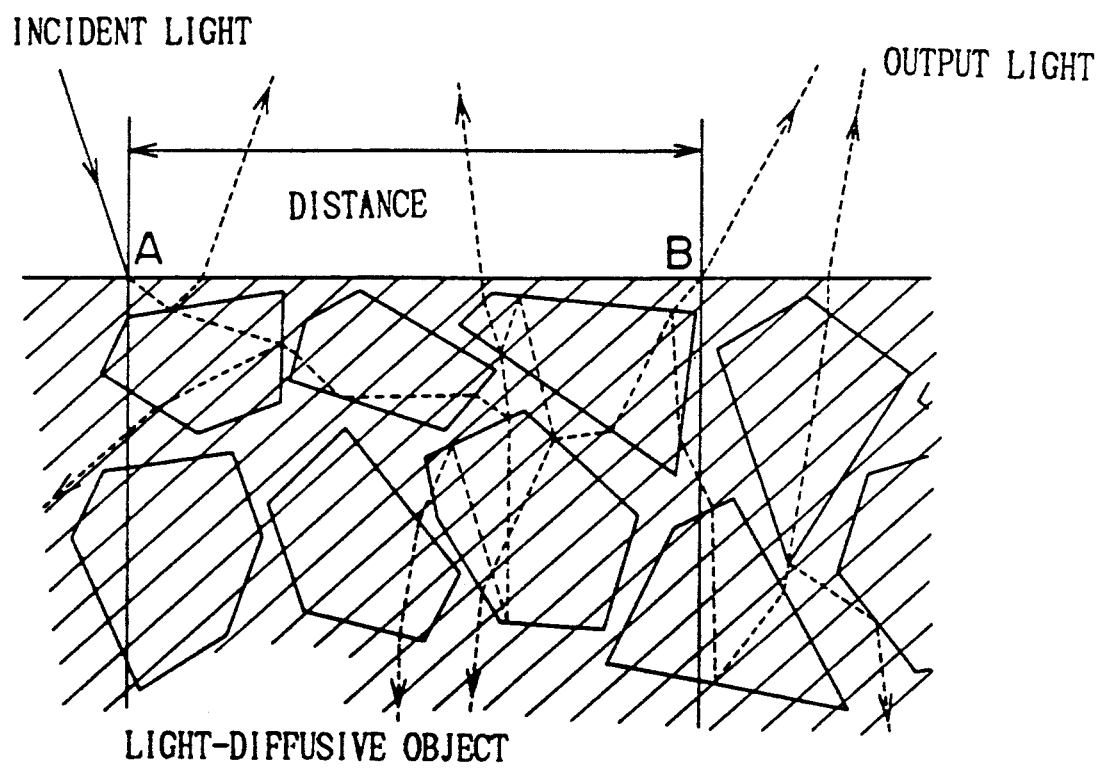
FIG. 9 is an explanatory view of the internal condition of a light-diffusive object where light is reflected and diffused.

FIG. 8 shows a graph where the percentage absorption $\%ABS_D$ of diffused light is corrected with the correction equations (1), (2), and (3). It is noted that the percentage absorption is standardized with the value at the wavelength 758 nm adjusted to zero. Referring to FIG. 8, $S_{Dn2}$ has a waveform similar to that of the percentage absorption n-$\%ABS_D$ of standardized diffused light. However, $S_{Dn1}$ has a waveform similar to that of the percentage absorption n-$\%ABS_T$ of standardized transmitted light, and $S_{Dn1.n2}$ has a waveform closest to that of the percentage absorption n-$\%ABS_T$.

In other words, the absorption spectrum of diffused light is prevented from being weakened or flattened through correction by means of the simple correction equations (1), (2), and (3) to succeed in having a waveform closer to that of the inherent absorption spectrum of transmitted light. Therefore, the spectrum waveform of a specimen of the same type of can be automatically corrected by means of the corrected spectrum waveforms SDn1, SDn2, and SDn1.n2.

Furthermore, the content of each component of a multicomponent object can be obtained from the corrected spectrum waveforms.

It is noted that the present invention is not limited to the above-mentioned embodiment. For example, although a living body is the measurement object in the above-mentioned embodiment, any other object can be selected for measurement so long as the object diffuses light. For example, a food object such as jerry, fruit, meat, fish and shellfish, or a plant object such as seed, seedling can be subject to measurement. It is further noted that a variety of modifications can be formed within the scope of the present invention. Although exponential type numeric equations are used for correction in the present invention, a variety of numeric equations such as Taylor-developed polynomial can be enumerated for providing the same effect as the correction equations.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method of determining an absorption spectrum, comprising the steps of:
   (a) applying light to a light applying point on a surface of an object;
   (b) receiving light which has passed through inside of said object at a light receiving point of said object;
   (c) detecting the intensity $I(\lambda)$ of light received at the light receiving point at various wavelengths to obtain the percentage absorption $\%ABS(\lambda)$ with the reference light intensity being $I_o(\lambda)$ according to an equation as follows:

$$\%ABS(\lambda) = \{I_o(\lambda) - I(\lambda)\}/I_o(\lambda);$$

and
   (d) determining a constant n such that the calculated result of a spectrum waveform $S(\lambda)$ using the equation $$S(\lambda) = exp[n \cdot \%ABS(\lambda)]$$

is about the same as the spectrum waveform of the inherent percentage absorption of said object;
   thereafter, when said object or a similar object calls for having its percentage absorption measured, substituting the calculated result of the spectrum waveform $S(\lambda)$ in step (d) to determine the spectrum waveform of the inherent percentage absorption of said object or said similar object at the time of measuring.

2. A method of determining an absorption spectrum, comprising the steps of:
   (a) applying light to a light applying point on a surface of an object;
   (b) receiving light which has passed through inside of said object at a light receiving point of said object;
   (c) detecting the intensity $I(\lambda)$ of light received at the light receiving point at various wavelengths to obtain the percentage absorption $\%ABS(\lambda)$ with the reference light intensity being $I_o(\lambda)$ according to an equation as follows:

$$\%ABS(\lambda) = \{I_o(\lambda) - I(\lambda)\}/I_o(\lambda);$$

and
   (d) determining constants $n_i$ ($i=1,2\ldots$) such that the calculated result of a spectrum waveform $S(\lambda)$ using the equation $$S(\lambda) = \sum_{i=1}^{K} exp[n_i \cdot \% ABS]$$

where K is a positive integer,
   is about the same as the spectrum waveform of the inherent percentage absorption of said object;
   thereafter, when said object or a similar object calls for having its percentage absorption measured, substituting the calculated result of the spectrum waveform $S(\lambda)$ in step (d) to determine the spectrum waveform of the inherent percentage absorption of said object or said similar object at the time of measuring.

3. A spectrometric measuring apparatus for a light-diffusive object, comprising:
   means for applying light to a light applying point on a surface of the object;
   means for receiving light which has passed through inside of said object at a light receiving point of said object;
   means for detecting the intensity $I(\lambda)$ of light received at the light receiving point at various wavelengths to obtain the percentage absorption $\%ABS(\lambda)$ with the reference light intensity being $I_o(\lambda)$ according to an equation as follows:

$$\%ABS(\lambda) = \{I_o(\lambda) - I(\lambda)\}/I_o(\lambda);$$

and
   means for calculating a spectrum waveform $S(\lambda)$ by assuming the spectrum waveform $S(\lambda)$ using one constant n according to an equation as follows:

$$S(\lambda) = exp[n \cdot \%ABS] \text{ and}$$

redefining said constant n such that the calculated result of the spectrum waveform $S(\lambda)$ is about the same as the spectrum waveform of the inherent percentage absorption of said object;
   said apparatus further comprises a substituting means for substituting the calculated result of the spectrum waveform $S(\lambda)$ output from said means for calculating to determine the spectrum waveform of the inherent percentage absorption of said object or a similar object while measuring the percentage absorption of said object or said similar object.

4. A spectrometric measuring apparatus for a light-diffusive object, comprising:
   means for applying light to a light applying point on a surface of an object;
   means for receiving light which has passed through inside of said object at a light receiving point of said object;
   means for detecting the intensity $I(\lambda)$ of light received at the light receiving point at various wavelengths to obtain the percentage absorption $\%ABS(\lambda)$ with the reference light intensity being $I_o(\lambda)$ according to an equation as follows:

$$\%ABS(\lambda) = \{I_o(\lambda) - I(\lambda)\}/I_o(\lambda);$$

and
   means for calculating a spectrum waveform $S(\lambda)$ by assuming the spectrum waveform $S(\lambda)$ using multiple constants $n_i$ ($i=1,2\ldots$) according to an equation as follows:

$$S(\lambda) = \sum_{i=1}^{K} exp[n_i \cdot \% ABS];$$

and, wherein K is a positive integer,
   and redefining said constants $n_i$ such that the calculated result of the spectrum waveform $S(\lambda)$ is about the same as the spectrum waveform of the inherent percentage absorption of said object;
   said apparatus further comprises a substituting means for substituting the calculated result of the spectrum waveform $S(\lambda)$ output from said means for calculating to determine the spectrum waveform of the inherent percentage absorption of said object or a similar object measuring the percentage absorption of said object or said similar object.

* * * * *

UNITED STATES PATENT AND TRADEMARK OFFICE
CERTIFICATE OF CORRECTION

PATENT NO.   : 5,333,610
DATED        : August 2, 1994
INVENTOR(S)  : Konomu HIRAO It is certified that error(s) appears in the above-identified patent and that said Letters Patent is hereby corrected as shown below:

Title page, item [30], change "4-63308" to --3-63308--.

Signed and Sealed this

Tenth Day of January, 1995

Attest:

BRUCE LEHMAN

Attesting Officer         Commissioner of Patents and Trademarks